United States Patent [19]

Van Gemert

[11] Patent Number: 5,244,602
[45] Date of Patent: Sep. 14, 1993

[54] PHOTOCHROMIC NAPHTHOPYRANS

[75] Inventor: Barry Van Gemert, Murrysville, Pa.

[73] Assignee: PPG Industries, Inc., Pittsburgh, Pa.

[21] Appl. No.: 624,816

[22] Filed: Dec. 3, 1990

[51] Int. Cl.$^5$ ............................................ C07D 311/92
[52] U.S. Cl. .................................... 252/589; 549/60; 549/389; 546/193; 546/196; 546/269; 544/126; 544/142; 544/143; 544/144; 524/84; 524/99; 524/102; 524/110
[58] Field of Search ............... 523/106; 549/389, 60; 546/193, 196, 269; 524/110, 111, 102, 99, 84; 252/589

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 549/389 |
| 4,215,010 | 7/1980 | Hovey et al. | 252/300 |
| 4,342,668 | 8/1982 | Hovey et al. | 252/586 |
| 4,563,458 | 1/1986 | Arno Widdig et al. | 514/253 |
| 4,637,698 | 1/1987 | Kwak et al. | 351/163 |
| 4,720,356 | 1/1988 | Chu | 252/586 |
| 4,806,534 | 2/1989 | Leonardi et al. | 514/233.5 |
| 4,816,584 | 3/1989 | Kwak et al. | 544/71 |
| 4,818,096 | 4/1989 | Heller et al. | 351/163 |
| 4,820,840 | 4/1989 | Ikegami et al. | 546/15 |
| 4,826,977 | 5/1989 | Heller et al. | 544/70 |
| 4,931,221 | 6/1990 | Heller et al. | 252/586 |
| 4,981,980 | 1/1991 | Giocobbe et al. | 549/345 |
| 5,066,818 | 11/1991 | Van Gemert et al. | 549/389 |
| 5,077,417 | 12/1991 | Schulte-Elte et al. | 549/389 |

FOREIGN PATENT DOCUMENTS

| | | |
|---|---|---|
| 246114 | 5/1987 | European Pat. Off. |
| 250193 | 6/1987 | European Pat. Off. |
| 294056 | 12/1988 | European Pat. Off. |
| 0403945A2 | 6/1989 | European Pat. Off. |
| 02-69471 | 3/1990 | Japan |

OTHER PUBLICATIONS

Padwa et al., J. Org. Chem., vol. 40, No. 8, 1975 1142.

*Primary Examiner*—C. Warren Ivy
*Assistant Examiner*—A. A. Owens
*Attorney, Agent, or Firm*—Irwin M. Stein

[57] ABSTRACT

Described are novel reversible photochromic naphthopyran compounds substituted on the naphthyl portion at the carbon atom juxtaposed to the oxygen of the pyran ring with, for example, an acetoxy group. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indolino)-oxazine type compounds, are also described.

32 Claims, No Drawings

PHOTOCHROMIC NAPHTHOPYRANS

DESCRIPTION OF THE INVENTION

The present invention relates to certain novel naphthopyran compounds. More particularly, this invention relates to novel photochromic naphthopyran compounds, and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, the photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −40° C. Irradiation of the compounds with visible light or upon raising the temperature to within the range of −10° C. to 0° C. is reported to reverse the coloration to a colorless state. U.S. Pat. No. 4,931,221 describes a series of spiropyrans in which two cyclopropyl groups are appended to the position adjacent to the oxygen in the pyran ring. U.S. Pat. No. 4,563,458 describes certain 2H-chromenes as precursors of certain chroman-4-aldehydes, which are reacted with certain amines to prepare 4-aminomethylene-chromans and -chromenes that are used in medicaments.

European Patent Publication 246,114 and U.S. Pat. No. 4,826,977 describe a series of photochromic spiropyrans in which a spiro-adamantane group is appended to the position adjacent to the oxygen in the pyran ring. U.S. Pat. No. 4,818,096 and European Patent Publication 250,193 describe photoreactive plastic lenses that are coated or impregnated with the photochromic spiropyrans of European Patent Publication 246,114 in combination with a blue photochromic benzopyran or naphthopyran having an aminophenyl substituent at the position adjacent to the oxygen in the pyran ring. European Patent Publication 294,056 describes a process for producing a polyurethane plastic having photochromic properties. Reversible cleavage photochromic compounds disclosed therein include a naphthopyran derivative in which the pyran ring is substituted at the 3-position of the pyran ring with di(p-methoxyphenyl) substituents. Japanese Patent Publication HEI 2(1990)-69471 describes spiropyran compounds in which a norbornylidene group is substituted at the position adjacent to the oxygen in the pyran ring.

Padwa et al in *J. Org. Chem.*, Volume 40, No. 8, 1975, page 1142, describes the investigation of photochemical reactions of 2,2-dimethylbenzopyran and related compounds, identifies the by-products and suggests pathways to the ring-opened color intermediates and the final non-colored phenolics. The color forms examined by the authors are reported as being unstable at room temperature. The authors do not suggest ways in which the stability of the examined compounds might be improved, nor any modification that might be made to the structure of the known pyran compounds.

The present invention relates to novel reversible photochromic naphthopyran compounds containing certain substituents on the naphtho portion of the naphthopyran at a carbon atom that is juxtaposed to the oxygen of the pyran ring. The absorption maxima of these compounds have been found to be higher than the corresponding unsubstituted compounds.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes have been of interest because of the potential safety features that such transparencies offer.

Ideal photochromic compounds for use in optical applications, such as conventional ophthalmic lenses, are those which possess (a) a high quantum efficiency for coloring in the near ultraviolet, (b) a low quantum yield for bleaching with visible light and (c) a relatively fast thermal fade at ambient temperature but not so rapid a thermal fade rate that the combination of visible light bleaching and thermal fade prevent coloring by the ultraviolet component of strong sunlight.

Compounds, such as 3,3-diphenyl-3H-naphtho[2,1-b]pyran, change color on exposure to the near ultraviolet; but, at room temperature and above, this compound bleaches too rapidly for use in an ophthalmic lens. The compound, 2,2-diphenyl-2H-naphtho[1,2-b] pyrin, also colors on exposure to near ultraviolet light at room temperature but does not bleach in a reasonable period of time.

In accordance with the present invention, there has been discovered certain novel reversible photochromic naphthopyran compounds. These compounds are substituted on the naphthyl portion at the carbon atom juxtaposed to the oxygen of the pyrin ring and exhibit a bathochromic shift of their absorption maximum without a loss of color intensity. In particular, 3,3-diaryl-3H-naphtho[2,1-b] pyrans (Graphic Formula I) that are appropriately substituted at the number five carbon atom have a high quantum efficiency for coloring in the near ultraviolet and an acceptable rate of fade and may be used in ophthalmic applications.

Naphthopyran compounds contemplated to be within the scope of the present invention may be represented by the following graphic formula I:

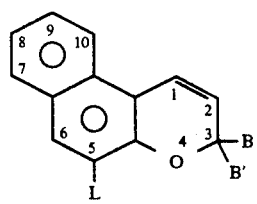

L in graphic formula I is the group, —W—T(Z)=Xg, wherein (1) W is selected from bivalent radicals of the group consisting of oxygen, carbon, nitrogen, oxygen-carbon, carbon-oxygen, carbon-nitrogen, nitrogen-carbon, and carbon-sulfur, as exemplified respectively by the following graphic formulae L-1 through L-8:

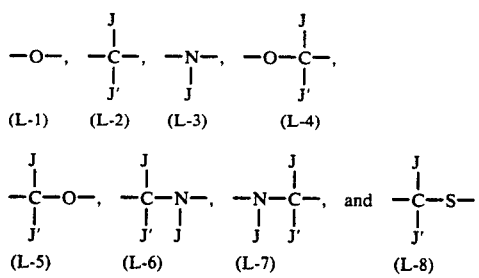

wherein J and J' are in each of the formulae L-1 to L-8 independently selected from the group consisting of hydrogen and $C_1$-$C_4$ alkyl, e.g., methyl, ethyl, propyl and butyl, or J and J' taken together is a single oxygen, e.g., —C(O)— (such as in formula L-2) or —O—C(O)— (such as in formula L-4);

(2) T is selected from group consisting of carbon and sulfur, and bears a partial positive charge;

(3) X is selected from the group consisting of oxygen, sulfur and —N—J", wherein J" is hydrogen, hydroxy, $C_1$-$C_4$ alkyl, $C_1$-$C_4$ alkoxy, or $C_1$-$C_4$ alkenyl, or when J" is $C_1$-$C_4$ alkyl or $C_1$-$C_4$ alkenyl, J" may combine with Z to form a nitrogen-containing heterocyclic ring;

(4) Z is selected from the group consisting of hydrogen, $C_1$-$C_4$ alkyl, $C_1$-$C_4$ alkenyl, $C_1$-$C_4$ monohaloalkyl, $C_1$-$C_4$ alkoxy($C_1$-$C_4$)alkyl, amino, $C_1$-$C_4$ mono- or dialkylamino, i.e., —N(J)J', the unsubstituted and substituted aryl groups, phenyl and naphthyl, and the unsubstituted and substituted heterocyclic groups, pyridyl, thienyl, furyl, piperidinyl, and furfuryl. The aryl and heterocyclic group substituents may be selected from the group consisting of $C_1$-$C_4$ alkyl, $C_1$-$C_4$ monohaloalkyl, $C_1$-$C_4$ polyhaloalkyl, $C_1$-$C_4$ alkoxy($C_1$-$C_4$)alkyl, $C_1$-$C_4$ alkoxy, and halogen. The halogen (or halo groups in the haloalkyl) substituent may be fluorine or chlorine;

(5) g is the integer 1 or 2 when X is sulfur, and is the integer 1 when X is oxygen or —N—J".

Preferably W is oxygen, carbon, or nitrogen (as represented by the graphic formulae L-1 through L-3, more preferably oxygen; T is carbon; X is oxygen; Z is $C_1$-$C_4$ alkyl, e.g., methyl, phenyl, or $C_1$-$C_4$ monoalkylamino, e.g., methylamino ($CH_3NH$—); and g is the integer one (1). More preferably, the group L is acetoxy ($CH_3C(O)O$—), benzoyloxy ($C_6H_5C(O)O$—), or methyl carbamyloxy ($CH_3NHC(O)O$—).

In graphic formula I, B and B' are each selected from the unsubstituted and mono, di or poly substituted aryl groups, phenyl and naphthyl, preferably mono- or di-substituted phenyl or naphthyl; the substituted or unsubstituted heterocyclic groups, pyridyl, thienyl, furyl, piperidinyl, and furfuryl; $C_1$-$C_4$ alkyl, $C_1$-$C_4$ haloalkyl, e.g., (chloro or fluoro) $C_1$-$C_4$ alkyl, $C_1$-$C_4$ alkoxy($C_1$-$C_4$)alkyl, $C_3$-$C_6$ cycloalkyl, $C_1$-$C_4$ alkoxy($C_3$-$C_6$)cycloalkyl, halo(chloro or fluoro) $C_3$-$C_6$ cycloalkyl, or B and B' may combine and taken together form adamantylidene.

The substituents for the aryl groups representing B and B' may be $C_1$-$C_4$ alkyl, $C_1$-$C_4$ haloalkyl, $C_1$-$C_4$ alkoxy, $C_1$-$C_4$ alkoxy($C_1$-$C_4$)alkyl, and halogen. The halogen (or halo group in the haloalkyl) may be chlorine or fluorine. Phenyl substituents may be located at the ortho, meta, and/or para positions. Typically, the phenyl substituent contains less than 3 substituents, i.e., zero (none), one or two substituents.

Substituents for the heterocyclic groups representing B and B' may be $C_1$-$C_4$ alkyl, $C_1$-$C_4$ haloalkyl, $C_1$-$C_4$ alkoxy, $C_1$-$C_4$ alkoxy($C_1$-$C_4$)alkyl, or halogen. The halogen (or halo group in the haloalkyl) may be chlorine or fluorine.

Preferably B and B' are each phenyl or substituted phenyl, e g., mono- or di-($C_1$-$C_4$)alkyl phenyl, such as methylphenyl; mono- or di-($C_1$-$C_4$)alkoxyphenyl, such as methoxyphenyl; chlorophenyl and fluorophenyl.

Compounds represented by graphic formulae I may be prepared by various synthetic routes. The particular route chosen will depend on the composition of "W". For example, compounds wherein "W" is oxygen (—O—) or oxygen-carbon (—O—C(J)J'), i.e., graphic formulae L-1 and L-4 may be prepared by reaction of 2,3-dihydroxynaphthalene with an appropriate reagent, e.g, acetic anhydride or an active halogen compound such as chloroacetone, which will yield the corresponding L-substituted hydroxy naphthalene e.g., 3-acetoxy-2-hydroxy naphthalene. The intermediate 3-substituted-2-hydroxy naphthalene may then be reacted further with the appropriate disubstituted, i.e., B,B'-substituted, propargyl alcohol, e.g., 1,1-diphenyl-2-propyn-1-ol, under acidic conditions to form compounds of graphic formula I.

In like manner, compounds wherein "W" corresponds to graphic formulae L-2, L-5, L-6 and L-8 may be prepared starting with 3-hydroxy-2-naphthoic acid. For example, the acid or corresponding acid ester may be reduced by several conventional methods to the corresponding 3-hydroxy-2-naphthaldehyde for conversion via the imine to 3(2-hydroxy) naphthylmethylamine. The acid ester can be reduced further with stronger reducing agents, for example, lithium aluminum hydride, to 3(2-hydroxy)naphthylmethanol. Both of these intermediates may be sequentially converted to the pyran by reaction first with a reagent such as a carboxylic acid anhydride or an alkylsulfonyl halide followed by reaction with a B,B'-substituted propargyl alcohol, as described above.

Compounds wherein "W" corresponds to graphic formulae L-3 and L-7 may be prepared by first selectively reacting the nitrogen of 3-amino-2-naphthol with reagents such as substituted or unsubstituted benzoyl halides, alkyl or aryl isocyanates, or active halogen bearing heterocycles, such as chloropyridine, to form 3-substituted-2-naphthols. These intermediates are converted via reaction with a propargyl alcohol to the corresponding pyran.

Compounds represented by graphic formula I may be used in those applications in which organic photochromic substances may be employed, such as for example optical lenses, e.g., ophthalmic and plano lenses, face shields, goggles, visors, camera lenses, windows, automotive windshields, aircraft and automotive transparencies, e.g., T-roofs, sidelights and backlights, plastic films and sheets, textiles and coatings, e.g., in coating compositions such as paints. Naphthopyrans represented by graphic formula I exhibit color changes from colorless to colors ranging from yellow to orange.

Of particular current interest are the following naphthopyrans:

(1) 5-acetoxy-3(3,4-dimethoxyphenyl),3(2-fluorophenyl)-3H-naphtho[2,1-b]pyran, (2) 5-methylcarbamoyloxy-3(3,4-dimethoxyphenyl),3(2-fluorophenyl)-3H-naphtho[2,1-b]pyran, (3) 5-acetoxy-3,(4-methoxyphenyl), 3(2-fluorophenyl)-3H-naphtho[2,1-b]pyran,
(4) 5-acetoxy-3(3,4-dimethoxyphenyl)-3-phenyl-3H-naphtho[2,1-b]-pyran, and
(5) 5-acetoxy-3,3(4-methylphenyl)-3H-naphtho[2,1-b]pyran.

Naphthopyrans described herein may be dissolved in common organic solvents such as benzene, toluene, chloroform, ethyl acetate, methyl ethyl ketone, acetone, ethyl alcohol, methyl alcohol, acetonitrile, tetrahydrofuran, dioxane, methyl ether of ethylene glycol, dimethylformamide, dimethylsulfoxide, morpholine and ethylene glycol. They may also be dispersed in fluorocarbons and in liquids containing water and/or alcohols.

The aforedescribed naphthopyran compounds may also be dissolved in solutions prepared with transparent organic host materials, e.g., transparent polymers (homopolymers or copolymers) or blends of such transparent polymers and optionally a suitable organic solvent, e.g., transparent polymers dissolved in one or more of the aforedescribed organic solvents. Examples of such solutions include a poly(vinyl acetate)-acetone solution, a nitrocellulose-acetonitrile solution, a poly(vinyl chloride)-methyl ethyl ketone solution, a poly(methylmethacrylate)-acetone solution, a cellulose acetate-dimethylformamide solution, a poly(vinyl pyrrolidone)-acetonitrile solution, a polystyrene-benzene solution and an ethyl cellulose-methylene chloride solution. The aforesaid photochromic solutions or compositions may be applied to a compatible host material, e.g., a transparent support, such as cellulose triacetate, polyethylene terephthalate or baryta paper and dried to obtain an article that will color on exposure to ultraviolet radiation and that will return to its original state by removing the source of ultraviolet radiation.

The naphthopyran compounds described herein (or compositions containing them) may be applied to or incorporated also within a coating composition applied to a compatible support; or applied to or incorporated within the article comprising the compatible host, e.g., a polymerized organic material such as a synthetic polymeric plastic host material.

The naphthopyrans described hereinabove may be incorporated in synthetic plastic materials customarily used for plastic optical lenses, both plano and ophthalmic. e.g., materials such as methyl methacrylate, polycarbonates and polymerizates prepared from CR-39 ® diallyl glycol carbonate monomer. Photochromic materials for photoreactive lenses preferably have the following stated desirable properties; namely, (a) a high quantum efficiency for coloring in the near ultraviolet, (b) a low quantum yield for bleaching with visible light, and (c) a relatively fast thermal fade at ambient temperatures, but not so fast that the photochromic material does not color in unfiltered sunlight at ambient temperatures. In addition, the aforesaid properties are desirably retained in conventional rigid synthetic plastic materials customarily used for ophthalmic and plano lenses when such materials have applied to or incorporated therein such naphthopyran compounds.

On irradiation of the compounds of graphic formula I with ultraviolet light, the naphthopyran ring opens reversibly at the carbon-oxygen bond between the number 3-carbon atom and the ring oxygen. The formation of the open form of the colorless compound is believed to be responsible for the coloring observed on exposure to ultraviolet light. The colored form of the photochromic compounds of graphic formula I will fade to the colorless state at normal ambient temperatures when not exposed to ultraviolet light.

Commercially available photoreactive inorganic glass ophthalmic lenses containing silver halide particles darken to a gray or brown color in sunlight. In order to duplicate this color change in a plastic lens using the organic photochromic naphthopyrans of graphic formula I, it is contemplated that such naphthopyrans be used in combination with other appropriate complementary organic photochromic materials so that together they produce the desired near neutral gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

Spiro(indolino) pyrido benzoxazine photochromic compounds described in U.S. Pat. No. 4,637,698 and spiro(indolino) naphthoxazines described in U.S. Pat. Nos. 3,562,172, 3,578,602, 4,215,010 and 4,342,668 are reported to color to colors ranging from purple to blue when activated, and these compounds may be used in admixture with or in conjunction with the yellow-orange novel naphthopyran photochromic compounds described in this application to obtain a near gray color when exposed to unfiltered sunlight. In addition, certain spiro(indolino)benzoxazines described in U.S. Pat. No. 4,816,584 color to shades of purple/blue when activated, and these compounds may be used also in admixture with or in conjunction with the photochromic naphthopyrans described in this application.

The aforesaid first mentioned spiro(indolino)-type compounds may be represented by the following graphic formula:

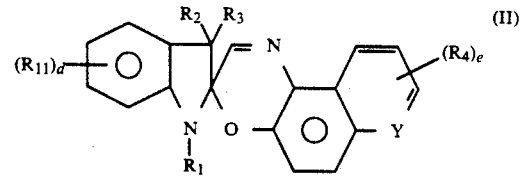

In the above graphic formula II, $R_1$ may be selected from the group consisting of $C_1-C_8$ alkyl, e.g., methyl, ethyl, n-propyl, isopropyl, butyl, etc., phenyl, phen(-$C_1-C_4$)alkyl, e.g., benzyl, naphth($C_1-C_4$)alkyl, e.g., 1-naphthylmethyl, allyl, acrylyl($C_2-C_6$)alkyl, methacrylyl- ($C_2-C_6$)alkyl, carboxy($C_2-C_6$)alkyl, e.g., $\beta$-carboxyethyl, $\gamma$-carboxypropyl, $\delta$-carboxybutyl, cyano($C_2-C_6$)alkyl, e.g., $\beta$-cyanoethyl, $\gamma$-cyanopropyl, $\beta$-cyanoisopropyl, and $\delta$-cyanobutyl, $C_1-C_4$ acyloxy($C_2-C_6$)alkyl, i.e., [$R_cC(O)OR_d$—, wherein $R_c$ is a $C_1-C_4$ alkyl and $R_d$ is a $C_2-C_6$ alkyl], e.g., acetoxyethyl, acetoxypropyl, propionyloxyethyl, acetoxybutyl, and propionyloxypropyl, hydroxy($C_2-C_6$)alkyl, e.g., hydroxyethyl, hydroxypropyl and hydroxybutyl, $(C_2H_4O)_m$·$CH_3$, wherein m is a number of from 1 to 6, and mono- and disubstituted phenyl, said phenyl substituents being selected from $C_1-C_4$ alkyl and $C_1-C_5$ alkoxy, e.g., methoxy, ethoxy, propoxy, butoxy and pentoxy. Preferably, $R_1$ is selected from the group consisting of $C_1$-$C_4$ alkyl, phenyl, benzyl, 1-naphth($C_1$-$C_2$)alkyl, such as 1-naphthylmethyl, carboxy($C_2$-$C_4$)alkyl, cyano($C_2$-$C_4$)alkyl, $C_1$-$C_4$ acyloxy($C_2$-$C_4$)alkyl, e.g., $C_1$-$C_4$ acyloxyethyl, hydroxy($C_2$-$C_4$)alkyl, and $(C_2H_4O)_m$ . $CH_3$, wherein m is a number of from 1 to 3, e.g., 2.

$R_2$ and $R_3$ of the above graphic formula II may each be selected from the group consisting of $C_1$-$C_5$ alkyl, phenyl, mono- and disubstituted phenyl, benzyl, or $R_2$ and $R_3$ may combine to form a cyclic ring selected from the group consisting of an alicyclic ring containing from 6 to 8 carbon atoms (including the spiro carbon atom), norbornyl and adamantyl. The aforesaid phenyl substituents may be selected from $C_1$-$C_4$ alkyl and $C_1$-$C_5$ alkoxy radicals. More particularly, $R_2$ and $R_3$ are each selected from $C_1$-$C_5$ alkyl, e.g., methyl, ethyl, propyl, butyl and pentyl, and phenyl. When one of $R_2$ or $R_3$ is a tertiary alkyl radical, such as tertiary butyl or tertiary amyl, the other is preferably an alkyl radical other than a tertiary alkyl radical.

Y in graphic formula II may be carbon or nitrogen. The number and type of non-hydrogen substituent groups represented by $R_4$ will vary depending upon whether Y is carbon or nitrogen. Generally, when Y is carbon each $R_4$ substituent may be selected from the group consisting of halogen, e.g., chloro, fluoro, or bromo, $C_1$-$C_5$ alkyl, $C_1$-$C_5$ alkoxy, e.g., methoxy, ethoxy, propoxy, butoxy and pentoxy, nitro, cyano, thiocyano, $C_1$-$C_4$ monohaloalkyl, e.g., $C_1$-$C_4$ monochloroalkyl, such as chloromethyl and chloroethyl, $C_1$-$C_2$ polyhaloalkyl, as, for example, trihaloalkyl such as trichloroalkyl or trifluoroalkyl, e.g., trifluoromethyl and 2,2,2-trifluoroethyl, and monoalkylamino or dialkylamino wherein the alkyl moiety of the alkylamino group contains from one to four carbon atoms, e.g., methylamino, ethylamino, propylamino, dimethylamino and diethylamino.

The letter "e" in graphic formula II is an integer of from 0 to 2, e.g., 1, and denotes the number of non-hydrogen $R_4$ substituents. In particular, when "e" is 1 or 2 and Y is carbon, each $R_4$ substituent may be selected from the group $C_1$-$C_2$ alkyl, $C_1$-$C_2$ alkoxy, chloro, fluoro, bromo, nitro, and trifluormethyl. When "e" is 0 (zero), there are no $R_4$ substituents and all of the aromatic carbon atoms in the naphtho group have their full complement of hydrogen atoms for the aromatic group shown.

When Y is nitrogen, each $R_4$ (non-hydrogen) substituent may be selected from $C_1$-$C_5$ alkyl, e.g., $C_1$-$C_2$ alkyl, $C_1$-$C_5$ alkoxy, e.g., $C_1$-$C_2$ alkoxy, and halogen, e.g., chloro, fluoro or bromo. Typically, "e" is 0 (zero) when Y is nitrogen and thus there are no $R_4$ substituents.

Each $R_{11}$ in graphic formula II may be selected from $C_1$-$C_5$ alkyl, halogen, $C_1$-$C_5$ alkoxy, nitro, cyano, $C_1$-$C_4$ monohaloalkyl, $C_1$-$C_4$ polyhaloalkyl, $C_1$-$C_8$ alkoxycarbonyl, and $C_1$-$C_4$ acyloxy, i.e., $R_cC(O)O—$, wherein $R_c$ is a $C_1$-$C_4$ alkyl, e.g., methyl. The letter "d" in graphic formula II represents an integer that may vary from 0 to 4, e.g., 0 to 2, such as 1 or 2, and denotes the number of non-hydrogen substituents. When "d" is 0 (zero), there are no $R_{11}$ substituents and all of the aromatic carbon atoms have their full complement of hydrogen atoms for the indole group.

More particularly, spiro(indolino) pyridobenzoxazines (when Y is nitrogen) may be represented by the following graphic formula:

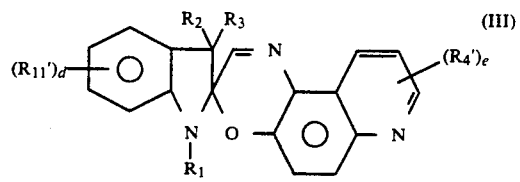

In graphic formula III, $R_1$, $R_2$ and $R_3$ are the same as defined with respect to graphic formula II. Each $R_4$ may be selected from $C_1$-$C_5$ alkyl, e.g., $C_1$-$C_2$ alkyl, $C_1$-$C_5$ alkoxy, e.g., $C_1$-$C_2$ alkoxy and halogen, e.g., chloro, fluoro or bromo. The letter "e" may be 0 or 1. Commonly, "e" is 0, and thus, there are no $R_4'$ substituents. When "e" is 1, the $R_4$ substituent may be located on any of the available carbon atoms of the pyrido moiety of the pyrido benzoxazine portion of the compound, i.e., at the 5', 6', 8' 9' or 10' positions, most usually at the 8', 9' or 10' positions.

Each $R_{11}'$ in graphic formula III may be selected from the group consisting of $C_1$-$C_5$ alkyl, e.g., methyl, ethyl, propyl, butyl and pentyl, halogen, e.g., chloro and fluoro, $C_1$-$C_5$ alkoxy, e.g., methoxy, ethoxy, propoxy, butoxy and pentoxy, nitro, cyano, $C_1$-$C_4$ monohaloalkyl, e.g., chloromethyl, fluoromethyl, chloroethyl, chloropropyl, etc., $C_1$-$C_4$ polyhaloalkyl, e.g., trihaloalkyl, $C_1$-$C_8$ alkoxycarbonyl, and $C_1$-$C_4$ acyloxy, i.e., $R_cC(O)O—$, wherein $R_c$ is a $C_1$-$C_4$ alkyl, e.g., methyl. An example of an acyloxy group is acetoxy. While any halogen, i.e., chlorine, bromine, iodine and fluorine may be used in respect to the aforesaid halogen or haloalkyl substituents, chlorine, fluorine and bromine, particularly chlorine and fluorine, are preferred for the halogen substituent and fluorine is preferred for the polyhaloalkyl substituent, e.g., trifluoromethyl, ($CF_3$). Preferably, $R_{11}'$ is selected from the group consisting of $C_1$-$C_2$ alkyl, chlorine, fluorine, $C_1$-$C_2$ trihaloalkyl, e.g., trihalomethyl such as trifluoromethyl and $C_1$-$C_5$ alkoxy.

The letter "d" in graphic formula III is an integer from 0 to 4, e.g., 0 to 2, such as 1 or 2. When "d" is 2 or more, each $R_{11}'$ substituent may be the same or different and in either case, are selected from the aforedescribed group. The $R_{11}'$ substituent(s) may be located on any of the available carbon atoms of the benzene ring of the indolino portion of the compound, i.e., at the 4, 5, 6 or 7 positions.

It is possible that photochromic organic substances of graphic formula III (and IV) may be a mixture of isomers due to the alternative directional mechanism by which intramolecular condensation occurs during formation of the starting indole reactant (Fischer's base). Indolization of 3-substituted phenylhydrazones can give rise to a 4-substituted indole, a 6-substituted indole, or mixtures thereof. Thus, when "d" is 1, the photochromic substance may be substituted at the 4 position on the indoline ring, at the 6 position of that ring or comprise a mixture of such isomers. When "d" is 2, the $R_{11}'$ substituents may be present at any combination of the 4, 5, 6, or 7 carbon atoms of the indoline ring and may comprise an isomeric mixture of such compounds, e.g., a mixture of compounds having substituents at the 4 and 5, 4 and 6, 5 and 6, 4 and 7, 5 and 7, and 6 and 7 positions of the indoline ring. Commonly, when "d" is 2 the $R_{11}'$ substituents are located at the 4 and 5, or 5 and 6 positions. Also contemplated are materials containing mixtures of such isomers, e.g., materials comprising 4 (and 6) and 5-substituted spiro(indolino) pyrido benzoxazines.

Non-limiting examples of spiro(indolino) pyridobenzoxazines of graphic formula III are described in Table 1. Such pyridobenzoxazines are those in which $R_1$, $R_2$, $R_3$, and $R_{11}'$ are as indicated in Table 1, the letter "e" is 0 (zero), and the letter "d" is 0, 1 or 2. A hyphen (-) indicates the absence of a non-hydrogen substituent.

TABLE 1

| Compound/ | $R_1$ | $R_2$ | $R_3$ | $R_{11}'$ | $R_{11}'$ |
|---|---|---|---|---|---|
| 1 | $CH_3$ | $CH_3$ | $CH_3$ | — | — |
| 2 | $CH_3$ | $CH_3$ | $CH_3$ | 4(6)-$CH_3$ | 5-$CH_3$ |
| 3 | $CH_3$ | $CH_3$ | $CH_3$ | 5-$OCH_3$ | — |
| 4 | $CH_3$ | $CH_3$ | $CH_3$ | 5-Cl | 6-$CH_3$ |
| 5 | $CH_3$ | $CH_3$ | $C_2H_5$ | — | — |
| 6 | $CH_3$ | $CH_3$ | $C_2H_5$ | 5-$CH_3$ | 4(6)-$CH_3$ |
| 7 | $CH_3$ | $C_2H_5$ | $C_2H_5$ | — | — |
| 8 | n-$C_4H_9$ | $CH_3$ | $C_2H_5$ | — | — |
| 9 | $CH_3$ | $CH_3$ | phenyl | — | — |
| 10 | $CH_3$ | phenyl | phenyl | — | — |
| 11 | $C_2H_5$ | $CH_3$ | $C_2H_5$ | 4(6)-$CH_3$ | 5-$CH_3$ |
| 12 | n-$C_4H_9$ | $CH_3$ | $C_2H_5$ | 5-$CH_3$ | (4)6-$CH_3$ |
| 13 | $CH_3$ | $CH_3$ | $CH_3$ | 5-$CH_3$ | (4)6-$CH_3$ |
| 14 | n-$C_3H_7$ | $CH_3$ | $CH_3$ | 5-$CH_3$ | — |
| 15 | i-$C_3H_7$ | $CH_3$ | $CH_3$ | 5-$OCH_3$ | — |
| 16 | n-$C_3H_7$ | $CH_3$ | $CH_3$ | 4(6)-$CH_3$ | 5-$CH_3$ |

Compound 2 in Table 1 may be named 1,3,3,4(and 6),5-pentamethylspiro-[indolino-2,3' [3H]pyrido [3,2-f] [1,4]benzoxazine]. Similarly, compound 6 in Table 1 may be named 1,3,4(and 6),5-tetramethyl-3-ethylspiro-[indolino-2,3' [3H] pyrido [3,2-f] [1,4]benzoxazine]. Other compounds in Table 1 may be similarly named taking into account the different substituents. Moreover, compounds derived from the description of graphic formula III may be similarly named by substituting the substituents described with respect to $R_1$, $R_2$, $R_3$, $R_4'$ and $R_{11}'$ for those found in the description and in Table 1. When the letter "e" is 1 or more, the $R_4'$ substituent(s) are given a prime (') designation. For nomenclature purposes, numbering of the pyrido benzoxazine portion of the molecule is counter clockwise starting with the nitrogen atom of the oxazine ring as the number 1' position. Numbering of the indolino portion of the molecule is counter clockwise starting with the nitrogen atom as the number 1 position.

Spiro(indolino)naphthoxazines that may be used in the practice of the present process may be represented by the following graphic formula:

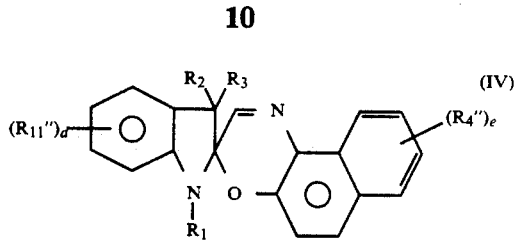

wherein $R_1$, $R_2$ and $R_3$ are the same as that described with respect to graphic formula II.

Each $R_4''$ substituent in graphic formula IV may be selected from the group consisting of halogen, e.g., chloro, fluoro, or bromo, $C_1$-$C_5$ alkyl, $C_1$-$C_5$ alkoxy (e.g., methoxy, ethoxy, propoxy, butoxy and pentoxy), nitro, cyano, thiocyano, $C_1$-$C_4$ monohaloalkyl, e.g., $C_1$-$C_4$ monochloroalkyl, such as chloromethyl and chloroethyl, $C_1$-$C_2$ polyhaloalkyl, as for example, trihaloalkyl, such as trichloroalkyl or trifluoroalkyl, e.g., trifluoromethyl and 2,2,2-trifluoroethyl, and monoalkylamino or dialkylamino, wherein the alkyl moiety of the alkylamino group contains from 1 to 4 carbon atoms, e.g., methylamino, ethylamino, propylamino, dimethylamino and diethylamino. More particularly, the $R_4'$ substituent may be selected from the group $C_1$-$C_2$ alkyl, $C_1$-$C_2$ alkoxy, chloro, fluoro, bromo, nitro and trifluormethyl. The letter "e" in graphic formula IV is an integer from 0 to 2, e.g., 1 or 2, and denotes the number of non-hydrogen R4'' substituents. When "e" is 0, there are no $R_4''$ substituents and all of the aromatic carbon atoms of the naphtho moiety of the molecule represented by formula IV have their full complement of hydrogen atoms for the naphtho group shown.

As in the case with graphic formula III, when "e" is 1, the $R_4''$ substituent may be located on any of the available carbon atoms of the naphtho moiety of the naphthoxazine portion of the molecule, i.e., at the 5', 6', 7' 8', 9' or 10' positions. Preferably, the $R_4''$ substituent is present on the 7', 8' or 9' carbon atoms. When "e" is 2, the $R_4''$ substituents may be same or different and in either case are selected from the above-described group. When "e" is 2, the $R_4''$ substituents are commonly located at the 7' and 9', or 8' and 10' positions. For nomenclature purposes, numbering of spiro(indolino) naphthoxazines is the same as that described with regard to the spiro(indolino) pyrido benzoxazines of graphic formula III. $R_{11}''$ and the letter "d" in graphic formula IV are the same as that described with respect to $R_{11}$ and d in graphic formula II.

Non-limiting examples of spiro(indolino) naphthoxazines selected from the description of graphic formula IV are described in Table 2. Such spiro(indolino) naphthoxazines are those in which $R_1$, $R_2$, $R_3$, $R_4''$ and $R_{11}''$ are as indicated in Table 2, the letter "d" is 0, 1 or 2 and the letter "e" is 1. As in Table 1, a hyphen (-) indicates the absence of a non-hydrogen substituent. In Table 2, all of the $R_4''$ substituents are at the 9' carbon position.

TABLE 2

| Compound/ | $R_1$ | $R_2$ | $R_3$ | $R_4''$ (9'-) | $R_{11}''$ | $R_{11}''$ |
|---|---|---|---|---|---|---|
| 1 | $CH_3$ | $CH_3$ | $CH_3$ | $OCH_3$ | — | — |
| 2 | $CH_3$ | $CH_3$ | $CH_3$ | $OCH_3$ | 5-$CH_3$ | (4)6-$CH_3$ |
| 3 | $CH_3$ | $CH_3$ | $CH_3$ | $OCH_3$ | 5-$OCH_3$ | — |
| 4 | $CH_3$ | $CH_3$ | $CH_3$ | $OCH_3$ | 5-Cl | (4)6-$CH_3$ |
| 5 | $CH_3$ | $CH_3$ | $C_2H_5$ | $OCH_3$ | — | — |
| 6 | $CH_3$ | $CH_3$ | $C_2H_5$ | $OCH_3$ | 5-$CH_3$ | (4)6-$CH_3$ |
| 7 | $CH_3$ | $C_2H_5$ | $C_2H_5$ | $OCH_3$ | — | — |
| 8 | n-$C_4H_9$ | $CH_3$ | $C_2H_5$ | $OCH_3$ | — | — |

TABLE 2-continued

| Compound/ | $R_1$ | $R_2$ | $R_3$ | $R_4''$ (9'-) | $R_{11}''$ | $R_{11}''$ |
| --- | --- | --- | --- | --- | --- | --- |
| 9 | $CH_3$ | $CH_3$ | phenyl | $OCH_3$ | — | — |
| 10 | $CH_3$ | phenyl | phenyl | $OCH_3$ | — | — |
| 11 | $CH_3$ | $p-C_6H_4OCH_3$ | $p-C_6H_4OCH_3$ | $OCH_3$ | — | — |
| 12 | $C_2H_5$ | $CH_3$ | $C_2H_5$ | $OCH_3$ | $5-CH_3$ | — |
| 13 | $n-C_4H_9$ | $CH_3$ | $C_2H_5$ | $OCH_3$ | $5-CH_3$ | — |

Compound 2 in Table 2 may be named 1,3,3,4(and 6),5-pentamethyl-9'-methoxy-spiro[indolino -2,3' [3H]-naphth [2,1-b][1,4]-oxazine]. Similarly, compound 6 in Table 2 may be named 1,3,4 (and 6),5-tetramethyl-3-ethyl-9'-methoxyspiro [indolino-2,3' [3H]-naphth [2,1-b][1,4]-oxazine. Other compounds in Table 2 can be similarly named taking into account the different substituents. Moreover, compounds derived from the description of graphic formula IV may be similarly named.

Spiro(indolino) benzoxazines compounds described in U.S. Pat. No. 4,816,584 may be represented by the following graphic formula V.

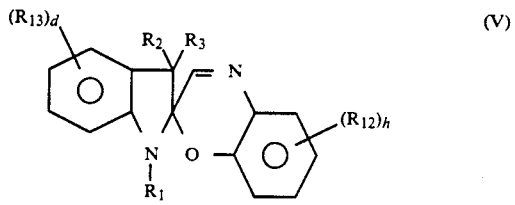

wherein $R_1$, $R_2$, $R_3$ and d are the same as described with respect to graphic formula II and $R_{12}$ and $R_{13}$ are each selected from the group consisting of $C_1$-$C_5$ alkyl, e.g., $C_1$-$C_2$ alkyl, $C_1$-$C_5$ alkoxy, e.g., $C_1$-$C_2$ alkoxy, preferably methoxy, and h is the integer 1 or 2.

When "h" is 1, the $R_{12}$ substituent may be located on any of the available carbon atoms of the benzene ring of the benzoxazine moiety, i.e., at the 5, 6, 7 or 8 positions. Preferably, the R12 substituent is located at the number 5, 6, or 7 carbon atom. When "h" is 2, the $R_{12}$ substituents may be the same or different and in either case are selected from the above-described group. When "h" is 2, the $R_{12}$ substituents are desirably located at the 5 and 7 or 6 and 8 positions.

Examples of spiro(indolino)benzoxazines within the scope of graphic formula V are listed in Table 3. Compound 1 may be named: 7-methoxy-1',3',3',4' (and 6'), 5'-pentamethylspiro- [2H-1,4-benzoxazine -2,2'-indoline]. Compounds 2-6 may be similarly named as substituted spiro(indolino) benzoxazines using the substituents described in Table 3 for such compounds. Moreover, compounds derived from the description of graphic formula V may be similarly named. In naming the spiro(indoline)benzoxazines, the IUPAC rules of organic nomenclature have been used. The positions of the indolino portion of the molecule have been numbered counterclockwise starting with the nitrogen atom as the number one (1) position, and are identified by a prime number, e.g., 3'. The positions of the benzoxazine portion of the molecule have been numbered clockwise starting with the oxygen atom as the number one (1) position.

TABLE 3

| Compound No. | $R_1$ | $R_2$ | $R_3$ | $R_{13}$ | $R_{13}$ | $R_{12}$ | $R_{12}$ |
| --- | --- | --- | --- | --- | --- | --- | --- |
| 1 | Me | Me | Me | 4(6)-Me | 5-Me | 7-OMe | — |

TABLE 3-continued

| Compound No. | $R_1$ | $R_2$ | $R_3$ | $R_{13}$ | $R_{13}$ | $R_{12}$ | $R_{12}$ |
| --- | --- | --- | --- | --- | --- | --- | --- |
| 2 | Me | Me | Me | 4(6)-Me | 5-Me | 7-OMe | 5-OMe |
| 3 | Me | Me | Me | 5-OMe | — | 7-OMe | 5-OMe |
| 4 | Me | Me | Me | 4(6)-Me | 5-Me | 7-OMe | 6-Ome |
| 5 | Me | Me | Et | — | — | 7-OMe | 5-OMe |
| 6 | nBu | Me | Me | — | — | 7-OMe | 5-OMe |

Key:
Me = methyl
nBu = n-butyl
Et = ethyl
OMe = methoxy

The naphthopyran compounds of the present invention may be combined with or used in conjunction with spiro(indolino) pyrido benzoxazine, or spiro(indolino) naphthoxazine compounds in amounts and in a ratio such that an organic host material to which the mixture of compounds is applied or in which they are incorporated exhibits a desired resultant color, e.g., a substantially neutral color such as shades of gray or brown, when activated with unfiltered sunlight, i.e., as near a neutral color as possible given the colors of the activated pyran and oxazine photochromic compounds. The relative amounts of the aforesaid oxazine and pyran compounds used will vary and depend in part upon the relative intensities of the color of the activated species of such compounds, and the ultimate color desired. Similarly, the naphthopyran compounds of the present invention may be combined with spiro(indolino)benzoxazine compounds in amounts and in a ratio such that an organic host material to which the mixture of compounds is applied or in which they are incorporated exhibits a near-brown color. Generally, the mole ratio of the aforedescribed spiro(indolino) oxazine compound(s) to the pyran compound(s) of the present invention will vary from about 1:3 to about 3:1, e.g., between about 1:1 and about 2:1.

Photochromic compounds of the present invention, mixtures of such compounds with other photochromic compounds, or compositions containing same (hereinafter "photochromic substances") may be applied to or incorporated into a host material by various methods described in the art. Such methods include dissolving or dispersing the substance within the host material, e.g., imbibition of the photochromic substance into the host material by immersion of the host material in a hot solution of the photochromic substance or by thermal transfer; providing the photochromic substance as a separate layer between adjacent layers of the host material, e.g., as a part of a polymer film; and applying the photochromic substance as part of a coating placed on the surface of the host material. The term "imbibition" or "imbibe" is intended to mean and include permeation of the photochromic substance alone into the host material, solvent assisted transfer absorption of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

Singlet oxygen quenchers that may be used as stabilizers include complexes of nickel(2+), i.e., $Ni^{2+}$, with an organic ligand, cobalt (III) tris-di-n-butyldithiocarbamate, cobalt (II) diisopropyldithiocarbamate, and nickel diisopropyldithiophosphate. Such singlet oxygen quenchers are used in stabilizing amounts.

Preferred are complexes of $Ni^{2+}$ such as [2,2-thiobis[4-(1,1,3,3-tetramethylbutyl) phenolato] (butylamine)] nickel, which is sold under the tradename of CYASORB UV 1084; nickel [O-ethyl(3,5-di-tert-butyl-4-hydroxybenzyl)] phosphonate, which is sold under the tradename IRGASTAB 2002; nickel dibutyldithiocarbamate, which is sold under the tradename RYLEX NBC; bis[2,2'-thiobis-4-(1,1,3,3-tetramethylbutyl)phenolato] nickel, which is sold under the tradename UV-CHEK AM 101; nickel di-isopropyl dithiophosphate and other $Ni^{2+}$ complexes sold under the tradenames of UV-CHEK AM 105, UV-CHEK 126, and UV-CHEK AM 205.

Hindered amine light stabilizers that may be used include bis(2,2,6,6-tetramethyl-4-piperidinyl) sebacate, which is sold under the tradename TINUVIN 770; bis(1,2,2,6,6-pentamethyl-4-piperidinyl) sebacate, which is sold under the tradename TINUVIN 765; di(1,2,2,6,6-pentamethyl-4-piperidinyl)butyl(3',5'-ditertiarybutyl-4-hydroxybenzyl)malonate, which is sold under the tradename TINUVIN 144; poly[(6-[(1,1,3,3-tetramethylbutyl)-amino]-1,3,5-triazine-2,4-diyl)-(6-[2,2,6,6-tetramethyl-4-piperidinyl]-amino-hexamethylene)], which is sold under the tradename CHIMASSORB 944; and poly[[6-(morpholino)-s-triazine-2,4-diyl][16-(2,2,6,6-tetramethyl-4-piperdyl)amino] hexamethylene], which is sold under the tradename CYASORB 3346. Other hindered amine light stabilizers that may be used are those sold under the tradename TINUVIN 622, SPINUVEX A-36 and HOSTAVIN TMN 20. Such stabilizers are used in stabilizing amounts.

The foregoing singlet oxygen quenchers and hindered amine light stabilizers may be used singly or in combination in amounts sufficient to enhance the light-fatigue resistance of the photochromic substance(s) described herein. Between 0.01 and about 5 percent by weight of the foregoing stabilizers may be used (alone or in combination) to improve the light fatigue resistance of the photochromic materials.

The polymer host material will usually be transparent, but may be translucent or even opaque. The polymer product need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material, e.g., materials suitable for optical applications, such as plano and ophthalmic lenses, windows, automotive transparencies, e.g., windshields, aircraft transparencies, plastic sheeting, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polycarbonates, poly(ethylene terephthalate), polystyrene, copoly(styrene-methyl methacrylate) copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a polycarbonate resin, such as the carbonate-linked resin derived from bisphenol A and phosgene, which is sold under the trademark, LEXAN; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80-90 percent diethylene glycol bis(allyl carbonate) and 10-20 percent vinyl acetate, particularly 80-85 percent of the bis(allyl carbonate) and 15-20 percent vinyl acetate, and copolymers with a polyurethan having terminal diacrylate functionality, as described in U.S. Pat. No. 4,360,653; cellulose acetate, cellulose propionate, cellulose butyrate, cellulose acetate butyrate, polystyrene and copolymers of styrene with methyl methacrylate, vinyl acetate and acrylonitrile.

Polyol (allyl carbonate) monomers which may be polymerized to form a transparent host material are the allyl carbonates of linear or branched aliphatic or aromatic liquid polyols, e.g., aliphatic glycol bis(allyl carbonate) compounds, or alkylidene bisphenol bis(allyl carbonate) compounds. These monomers can be described as unsaturated polycarbonates of polyols, e.g. glycols. The monomers can be prepared by procedures well known in the art, e.g., methods described in U.S. Pat. Nos. 2,370,567 and 2,403,113.

The aforedescribed polyol (allyl carbonate) monomers may be represented by the graphic formula:

 (VI)

wherein R is the radical derived from an unsaturated alcohol and is commonly an allyl or substituted allyl group, R' is the radical derived from the polyol, and n is a whole number from 2-5, preferably 2. The allyl group (R) may be substituted at the 2 position with a halogen, most notably chlorine or bromine, or an alkyl group containing from 1 to 4 carbon atoms, generally a methyl or ethyl group. The R group may be represented by the graphic formula:

 (VII)

wherein $R_o$ is hydrogen, halogen, or a $C_1$-$C_4$ alkyl group. Specific examples of R include the groups: allyl, 2-chloroallyl, 2-bromoallyl, 2-fluoroallyl, 2-methylallyl, 2-ethylallyl, 2-isopropylallyl, 2-n-propylallyl, and 2-n-butylallyl. Most commonly R is the allyl group, $H_2C=CH-CH_2-$.

R' is a polyvalent radical derived from the polyol, which can be an aliphatic or aromatic polyol that contains 2, 3, 4 or 5 hydroxy groups. Typically, the polyol contains 2 hydroxy groups, i.e., a glycol or bisphenol. The aliphatic polyol can be linear or branched and contain from 2 to 10 carbon atoms. Commonly, the aliphatic polyol is an alkylene glycol having from 2 to 4 carbon atoms or a poly($C_2$-$C_4$) alkylene glycol, i.e., ethylene glycol, propylene glycol, trimethylene glycol, tetramethylene glycol, or diethylene glycol, triethylene glycol, etc.

The aromatic polyol can be represented by the graphic formula:

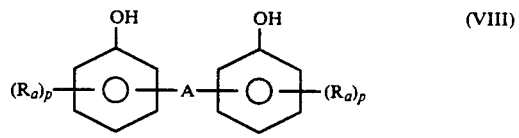 (VIII)

wherein A is a bivalent radical derived from an acyclic aliphatic hydrocarbon, e.g., an alkylene or alkylidene radical, having from 1 to 4 carbon atoms, e.g., methylene, ethylene, and dimethylmethylene (isopropylidene), $R_a$ represents lower alkyl substituents of from 1 to 3 carbon atoms and halogen, e.g., chlorine and bromine, and p is the integer 0, 1, 2, or 3. Preferably, the hydroxyl group is in the ortho or para position.

Specific examples of the radical R' include: alkylene groups containing from 2 to 10 carbon atoms such as ethylene, $(-CH_2-CH_2-)$, trimethylene, methylethylene, tetramethylene, ethylethylene, pentamethylene, hexamethylene, 2-methylhexamethylene, octamethylene, and decamethylene; alkylene ether groups such as $-CH_2-O-CH_2-$, $-CH_2CH_2-O-CH_2CH_2-$, $-CH_2-O-CH_2-CH_2-$, and $-CH_2CH_2CH_2-O-CH_2CH_2CH_2-$; alkylene polyether groups such as $-CH_2CH_2-O-CH_2CH_2-O-CH_2CH_2-$, and $-CH_2CH_2CH_2-O-CH_2CH_2CH_2-O-CH_2CH_2CH_2-$; alkylene carbonate and alkylene ether carbonate groups such as $-CH_2CH_2-O-CO-O-CH_2CH_2-$ and $-CH_2CH_2-O-CH_2CH_2-O-CO-O-CH_2CH_2-O-CH_2CH_2-$; and isopropylidene bis(para-phenyl), i.e.,

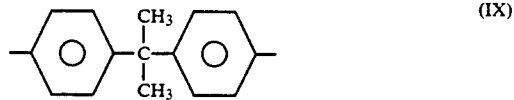 (IX)

Most commonly, R' is $-CH_2CH_2-$, $-CH_2CH_2-O-CH_2CH_2-$, or $-CH_2CH_2-O-CH_2CH_2-O-CH_2CH_2-$.

Specific non-limiting examples of polyol (allyl carbonate) monomers include ethylene glycol bis(2-chloroallyl carbonate), ethylene glycol bis(allyl carbonate), diethylene glycol bis(2-methallyl carbonate), diethylene glycol bis(allyl carbonate), triethylene glycol bis(allyl carbonate), propylene glycol bis(2-ethylallyl carbonate), 1,3-propanediol bis(allyl carbonate), 1,3-butanediol bis(allyl carbonate), 1,4-butanediol bis(2-bromoallyl carbonate), dipropylene glycol bis(allyl carbonate), trimethylene glycol bis(2-ethylallyl carbonate), pentamethylene glycol bis(allyl carbonate), and isopropylidene bisphenol bis(allyl carbonate).

Industrially important polyol bis(allyl carbonate) monomers which may be utilized in the invention herein contemplated are:

 (X)

Triethylene Glycol bis(Allyl Carbonate)

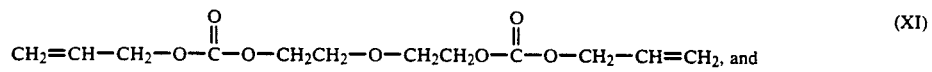 (XI)

Diethylene Glycol bis(Allyl Carbonate)

-continued

Ethylene Glycol bis(Allyl Carbonate)

Diethylene glycol bis(allyl carbonate) is preferred.

Because of the process by which the polyol(allyl carbonate) monomer is prepared, i.e., by phosgenation of the polyol (or allyl alcohol) and subsequent esterification by the allyl alcohol (or polyol), the monomer product can contain related monomer species in which the moiety connecting the allyl carbonate groups contains one or more carbonate groups. These related monomer species can be represented by the graphic formula:

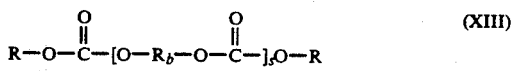

(XIII)

wherein R is as defined above, $R_b$ is a bivalent radical, e.g., alkylene or phenylene, derived from a diol, and s is a whole number from 2 to 5. The related monomer species of diethylene glycol bis(allyl carbonate) can be represented by the graphic formula,

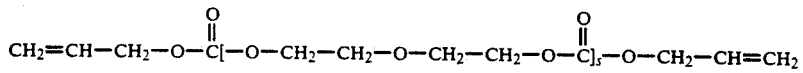

(XIV)

wherein s is a whole number from 2 to 5. The polyol (allyl carbonate) monomer can typically contain from 2 to 20 weight percent of the related monomer species and such related monomer species can be present as mixtures, i.e., mixtures of the species represented by s being equal to 2, 3, 4, etc.

In addition, a partially polymerized form of the polyol (allyl carbonate) monomer, i.e., prepolymer, can be used. In that embodiment, the monomer is thickened by heating or partially polymerized by using small, e.g., 0.5-1.5 parts of initiator per hundred parts of monomer (phm), to provide a non-gel containing, more viscous monomeric material.

As used in the present description and claims, the term polyol(allyl carbonate) monomer or like names, e.g., diethylene glycol bis(allyl carbonate), are intended to mean and include the named monomer or prepolymer and any related monomer species contained therein.

Polyfunctional acrylate monomers that may be used to prepare synthetic polymeric host materials are esterification Products of an acrylic acid moiety selected from the group consisting of acrylic acid and methacrylic acid, and a polyol, e.g., a diol, a triol or tetracarbinol. More particularly, the polyfunctional acrylate monomer may be represented by the following graphic formula:

$(CH_2=C(R_t)-C(O))-_nR''$  (XV)

wherein $R_t$ is hydrogen or methyl, n is the number 2, 3, or 4, and R'' is the multivalent radical, i.e., a bivalent, trivalent or quadravalent radical, remaining after removal of the hydroxy groups from a polyol, having from 2 to 4 hydroxy groups, e.g., a diol, a triol or tetracarbinol respectively. More particularly, $R_t$ is hydrogen or methyl, and n is 2 or 3, more usually 2.

R'' may be selected from the group consisting of alpha, omega $C_2$-$C_8$ glycols, cyclohexane diol, diethylene glycol, triethylene glycol, tetraethylene glycol, dipropylene glycol, $C_2$-$C_5$ triols and pentaerythritol. Examples of such polyols include ethylene glycol, trimethylene glycol, 1,4-butane diol, 1,5-pentane diol, 1,6-hexane diol, propylene glycol, trimethylol propane, glycerol and the like.

Examples of polyfunctional acrylate monomers, such as diacrylates and triacrylates, include: ethylene glycol diacrylate, ethylene glycol dimethacrylate, 1,2-propane diol diacrylate, 1,3-propane diol diacrylate, 1,2-propane diol dimethacrylate, 1,3-propane diol dimethacrylate, 1,4-butane diol diacrylate, 1,3-butane diol dimethacrylate, 1,4-butane diol dimethacrylate, 1,5-pentane diol diacrylate, 2,5-dimethyl-1,6-hexane diol dimethacrylate, diethylene glycol diacrylate, diethylene glycol dimethacrylate, triethylene glycol dimethacrylate, trimethylol propane trimethacrylate, tetraethylene glycol diacrylate, tetraethylene glycol dimethacrylate, dipropylene glycol diacrylate, dipropylene glycol dimethacrylate, trimethylol propane triacrylate, glycerol triacrylate, glycerol trimethacrylate, pentaerythritol triacrylate, pentaerythritol dimethacrylate, pentaerythritol tetraacrylate, pentaerythritol tetramethacrylate and mixtures of such acrylate monomers.

A portion of the polyfunctional acrylate monomer may be replaced with a monofunctional copolymerizable monomer containing the vinyl ($CH_2=CH$-) grouping. Such compatible monomers include monofunctional acrylic and methacrylic acid esters, and vinyl esters of $C_2$-$C_6$ carboxylic acids, i.e., vinyl carboxylates. Preferably, the copolymerizable monomer is a non-aromatic, e.g., non-benzenoid, containing monomer. Monofunctional acrylic or methacrylic ester monomers may be graphically illustrated by the following formula, $CH_2=C(R_t)-C(O)-O-R'''$  (XVI)

wherein $R_t$ is hydrogen or methyl, and R''' is selected from the group consisting of $C_1$-$C_{12}$, e.g., $C_1$-$C_8$, alkyl, $C_5$-$C_6$ cycloalkyl, glycidyl and hydroxyethyl. Preferably, R''' is a $C_1$-$C_4$ alkyl, e.g., methyl or cyclohexyl.

Examples of monofunctional acrylic acid type monomers include, for example, the acrylic and methacrylic acid esters of alkanols such as methanol, ethanol, propanol, butanol, pentanol, hexanol, heptanol and octanol, e.g., methyl acrylate, methyl methacrylate, ethyl acrylate and ethyl methacrylate, cycloalkanols such as cyclopentanol and cyclohexanol, glycidol (3-hydroxy propylene oxide, (d, 1, d1)) and ethylene glycol. Examples of vinyl carboxylates include vinyl acetate, vinyl propionate, vinyl butyrate and vinyl valerate. In addition to and/or in place of the aforedescribed monofunctional copolymerizable monomer, monofunctional allylic and difunctional allylic copolymerizable compatible monomers may also replace a portion of the polyfunctional acrylate monomer. Monofunctional allylic monomers contemplated include allyl esters of $C_2$-$C_6$ carboxylic acids, $C_1$-$C_6$ allyl ethers and other copolymerizable allyl compounds. Preferably the monofunctional allylic monomer is a non-aromatic compound. Difunctional allylic copolymerizable monomers contemplated herein are the polyol (allyl carbonates) monomers of graphic formula VI.

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more compound applied or incorporated, the greater is the color intensity. Generally, the amount of each photochromic substance incorporated into or applied to the host material may range from about 0.01 or 0.05 to about 10 to 20 percent by weight. More typically, the amount of photochromic substance(s) incorporated into or applied to the host material will range from about 0.01 to about 2 weight percent, more particularly, from about 0.01 to about 1 weight percent, e.g., from about 0.1 or 0.5 to about 1 weight percent, based on the weight of the host material.

The present invention is more particularly described in the following examples which are intended as illustrative only, since numerous modifications and variations therein will be apparent to those skilled in the art.

EXAMPLE 1

A reaction flask was charged with 15 milliliters (ml) of methylene chloride and 6.4 grams (0.04 mole) of 2,3-dihydroxynaphthalene. Acetic anhydride (4.0 grams) was added to the reaction flask with stirring. The reaction flask was cooled with an ice bath and 4.05 ml of triethylamine were added to the reaction flask over a 5 minute period. The reaction mixture was allowed to set at room temperature for 1.5 hours and then poured into dilute aqueous hydrochloric acid. The white solid product that precipitated was filtered, washed with methylene chlorine to remove diacylated material, washed with water, and then dried. The product (6.0 grams) was confirmed as 3-acetoxy-2-hydroxynaphthalene by nuclear magnetic resonance (NMR) spectroscopy.

2.0 grams (g) of the aforedescribed product, 3-acetoxy-2-hydroxynaphthalene, were mixed with 2.0 g of 1,1-diphenyl-2-propyn-1-ol in 75 ml of benzene. A catalytic amount of p-toluene sulfonic acid was added and the mixture heated with stirring to 60° C. After 2 hours, the reaction mixture was cooled to room temperature, poured into dilute aqueous sodium hydroxide and the resulting benzene phase separated from the aqueous phase. The benzene phase was washed with water, dried over anhydrous sodium sulfate and the benzene removed on a rotary evaporator. The resultant oil product was mixed with a hexane-ether mixture to induce crystallization. The resultant product was filtered, washed with a small amount of hexane, and dried. The product (2.5 grams) melted at 139°-141° C. An NMR spectrum confirmed the product to be 5-acetoxy-3,3-diphenyl-3H-naphtho[2,1-b]pyran.

EXAMPLE 2

A reaction flask was charged with 3.2 g (0.02 mole) of 2,3-dihydroxynaphthalene and 0.4 mole of 2-chloropyridine and the mixture heated at 150° C. for 2 hours. The resultant mixture was cooled and placed in a separatory funnel containing dilute aqueous sodium hydroxide and methylene chloride. The aqueous phase was made acidic by the addition of dilute hydrochloric acid and the resultant solution then made slightly basic by the addition of aqueous sodium bicarbonate. The solid which crystallized from the aqueous solution was washed with hot water until the starting material (2,3-dihydroxynaphthalene) was removed. The remaining solid product (2.5 g) was confirmed to be 3(2-pyridyloxy)-2-hydroxynaphthalene by NMR spectroscopy.

The above prepared 3(2-pyridyloxy)-2-hydroxynaphthalene (2.0 g) was mixed with 75 ml of toluene and 2.0 g of 1,1-diphenyl-2- propyn-1-ol. A molar equivalent (based on the 3(2-pyridyloxy)-2-hydroxynaphthalene reactant) of p-toluene sulfonic acid (1.6 g) was added to the reactant mixture which was heated to 60° C. with stirring. After 15 minutes, the mixture was cooled, poured into dilute aqueous sodium hydroxide and the toluene layer separated from the aqueous phase. The toluene layer was washed with water, dried over anhydrous sodium sulfate and the toluene removed on a rotary evaporator. The resultant oil product was column chromatographed on silica using a 1:1 mixture of hexane:chloroform as the elutant. The photochromic fractions were combined and the material re-chromatographed on a medium pressure column of reverse phase (RP-8) silica using a 2:1 mixture of acetonitrile:water as the elutant. The photochromic fractions were combined, rotovaped to remove acetonitrile and the product extracted into methylene chloride. The methylene chloride was then removed on a rotary evaporator and the resultant oil induced to crystallize by cooling in a mixture of hexane and diethyl ether. The product was filtered, washed with a small amount of hexane, and dried. The product (0.8 g) melted at 124°-125.5° C. NMR spectroscopy confirmed the product to be 5(2-pyridyloxy)-3,3-diphenyl-3H naphtho[2,1-b]pyran.

EXAMPLE 3

In accordance with the procedure of Example 1, 3-acetoxy-2-hydroxynaphthalene (2.0 g, 0.01 mole) was reacted with 1-phenyl-1-p-methoxyphenyl-2-propyn-1-ol (2.4 grams). The product was chromatographed twice over silica using a 2:1 mixture of hexane:ethyl acetate as elutant. The product was an oil. The product was confirmed as 5-acetoxy-3-phenyl-3-p-methoxy phenyl-3H-naphtho[2,1-b]pyran by NMR spectroscopy.

EXAMPLE 4

A reaction flask was charged with 50 ml of methylene chloride, 6.4 g (0.4 mole) of 2,3-dihydroxynaphthalene and 0.4 mole of benzoyl chloride. The stirred mixture was cooled in an ice bath and a slight excess of triethylamine added dropwise to the reaction flask. The ice bath was removed and the reaction mixture stirred for one hour. Dilute hydrochloric acid (50 ml) was added to the reaction flask and the resultant mixture stirred. A solid precipitated and the contents of the reaction flask were filtered. The filter cake (solid precipitate) was washed with a small amount of methylene chloride to remove the di-benzoylated product. The remaining solid product was washed with water and dried to yield 7.9 g of product, i.e., 3-benzoyloxy-2-hydroxynaphthalene.

12 g of phenyl-p-methoxyphenyl ketone was mixed in 75 ml of tetrahydrofuran at room temperature with a 20 percent excess of sodium acetylide, which was obtained as an 18 percent solution in xylene/mineral oil. The mixture was allowed to set for 24 hours with stirring while being protected from moisture. Dilute hydrochloric acid was added to the reaction mixture and the organic layer separated. The aqueous phase was extracted with ether and the extracts combined, dried and rotovaped. The resultant oil was chromatographed on silica using a 2:1 mixture of hexane:ethyl acetate as elutant to yield 9.5 grams of a light yellow oil. NMR spectroscopy confirmed the product to be 5-benzyloxy-1-phenyl-1-p-methoxy phenyl-3-propyn-1-ol.

2.8 g of the aforesaid light yellow oil and 3 g of 3-benzoyloxy-2-hydroxynaphthalene were mixed in benzene in the presence of a trace amount of toluene sulfonic acid catalyst. The reaction mixture was heated for 45 minutes at reflux. Subsequently, the reaction mixture was cooled, washed with aqueous sodium hydroxide, and the organic phase separated from the aqueous phase. The residual oil was chromatographed on silica using a 4:1 mixture of hexane:ethyl acetate as elutant. The photochromic fractions were collected and crystallized from a hexane-ether mixture. The resultant crystals were dried, washed with a slight amount of hexane and dried. The product (2.5 g) was a yellow-white crystal which melted at 125°–126° C. NMR spectroscopy confirmed the product to be 5-benzoyloxy-3-phenyl-3-p-methoxy phenyl-3H-naphtho[2,1-b]pyran.

EXAMPLE 5

The procedure of Example 4 was repeated using 1,1-diphenyl-3-propyn-1-ol. The reaction mixture was heated in benzene with a small amount of toluene sulfonic catalyst for 1 hour. The reaction mixture was a dark orange color. The reaction mixture was cooled and the solid reactant that had not dissolved, i.e., 3-benzoyloxy-2-hydroxynaphthalene, removed by filtration. The benzene solution was washed with 5 percent aqueous sodium hydroxide and the benzene solvent removed on a rotary evaporator. The residual oil was column chromatographed on silica using a 4:1 hexane:ethyl acetate mixture as the elutant. The photochromic fractions were combined and induced to crystallize by cooling in a hexane-diethyl ether mixture. The solid product was filtered, washed with a little fresh hexane-diethyl ether and dried. 2.8 g of product was obtained, which was confirmed by NMR spectroscopy to be 5-benzoyloxy-3,3-diphenyl-3H-naphtho[2,1-b]pyran.

EXAMPLE 6

33.5 grams of 2,3-dihydroxynaphthalene was reacted with a molar equivalent (12 g) of methyl isocyanate in methylene chloride in the presence of a catalytic amount of dimethylaminopyridine (DMAP). The reaction solution initially exothermed to 40° C. and then was allowed to cool back to room temperature. The reaction solution was then stirred for one hour. Subsequently, the reaction mixture was filtered to remove solid, which was washed with methylene chloride and then air dried. The product was confirmed by NMR spectroscopy to be 3-methylcarbamyloxy-2-hydroxynaphthalene.

Three grams of the product prepared as above was reacted with 2 grams of 1,1-diphenyl-2-propyn-1-ol in benzene using p-toluene sulfonic acid as the catalyst. The reaction mixture was heated to reflux for two hours and then cooled and washed with dilute aqueous sodium hydroxide. Solids present in the reaction mixture were removed by filtration, the aqueous phase separated from the organic phase, and the organic phase rotovaped to remove benzene solvent. The residue was taken up in ether and filtered to remove more solid. These solids were shown to be the material 3-methylcarbamyloxy-2-hydroxynaphthalene. The ether was removed on a rotary evaporator and the resultant solid washed with a 50:50 mixture of hexane:diethyl ether to yield 0.75 g of a solid product, which was confirmed by NMR spectroscopy to be 5-methylcarbamyloxy-3,3-diphenyl-3H-naphtho[2,1-b]pyran.) The melting point of the product was determined to be 154°–156° C.

EXAMPLE 7

Two grams of 3-methyl carbamyloxy-2-hydroxynaphthalene and 4 grams of crude 1-phenyl-1-p-methoxyphenyl-3-propyn-1-ol were suspended in 100 ml toluene. The mixture was refluxed for one hour in the presence of a catalytic amount of p-toluene sulfonic acid. The reaction mixture was cooled and washed with dilute aqueous sodium hydroxide and then with water. The organic phase was separated and toluene removed on a rotary evaporator. The remaining crude oil was chromatographed on silica using as elutants first hexane:ethyl acetate (2:1) and then chloroform:hexane (1:1). The photochromic fractions were combined, crystallized from diethyl ether, and the crystals suctioned filtered. The filtered crystals were washed with diethyl ether. The crystalline product was light tan in color and had a melting point of 150°–153° C. NMR spectroscopy confirmed the product to be 5-methylcarbamyloxy-3-phenyl-3-methoxyphenyl-3H-naphtho[1,2-b]pyran.

EXAMPLE 8

2,3-dihydroxynaphthalene (6.4 g), chloroacetone (0.04 mole, 3.7 g) and anhydrous powdered potassium carbonate (0.04 mole, 5.5 g) were added to 150 ml of anhydrous acetone and mixed under reflux for six hours. The mixture was cooled and the acetone removed on a rotary evaporator. Water was added and the resultant solid broken up and filtered. The filter cake was washed with hot water to remove any unreacted dihydroxynaphthalene reactant and dried. The dried product (6.8 g) was identified by NMR spectroscopy to be a mixture of 2-hydroxy-3-(2-oxy)-propoxy naphthalene and 2-hydroxy-2-methyl-1,4-naphthodioxan. Two grams of this mixture, 2g of 1,1-diphenyl-2-propyn-1-ol, and a catalytic amount of p-toluene sulfonic acid were mixed in 100 ml of toluene. The mixture was refluxed for 2 hours, cooled, washed with dilute aqueous sodium hydroxide, and filtered. The toluene solution was washed twice with water and then the toluene removed on a rotary evaporator. On addition of diethyl ether, the product crystallized. The product crystals were filtered, washed with fresh diethyl ether, and dried. The melting point of the crystals was determined to be 184°–186° C. and NMR spectroscopy confirmed the structure to be 5-(2-acetonyloxy)-3,3-diphenyl-3H-naphtho[2,1-b]pyran.

EXAMPLE 9

Ten grams of 4,4'-dimethylbenzophenone was added to 100 ml of tetrahydrofuran containing a small amount of lithium aluminum hydride. A slight excess (14 g) of sodium acetylide as an 18% solution in xylene-mineral oil was added to the ketone and the mixture stirred at room temperature. After three hours, no ketone was observed in the reaction mixture. Dilute aqueous hydrochloric acid (50 ml) was added to the reaction mixture and the organic layer separated, then washed with water, and dried. The aqueous phase was washed with ether and the ether extract washed with water and dried. The organic fractions were combined and solvent removed on a rotary evaporator to give the crude acetylinic alcohol 1,1-di-p-methylphenyl-3-propyn-1-ol as a light tan oil.

Three grams of the foregoing oil and 2 grams of 3-acetoxy-2-hydroxynaphthalene were mixed in benzene and heated to reflux with stirring in the presence of a trace amount of toluene sulfonic acid. The reaction mixture was heated at reflux for one hour after which the reaction mixture was poured into dilute aqueous sodium hydroxide. The benzene layer was separated, washed with water and solvent removed on a rotary evaporator. The resultant product was an oil which was column chromatographed on silica using a 2:1 hexane:ethyl acetate mixture as elutant. The photochromic fractions were combined and crystallized from a hexane/ether mixture by cooling in a dry ice-acetone mixture. The crystals were suction filtered and dried. The product was confirmed by NMR spectroscopy to be 5-acetoxy-3,3-di(p-methylphenyl)-3H-naphtho[2,1-b]pyran. The product has a melting point of 118°-119° C.

EXAMPLE 10

Chloroacetic anhydride (8.5 g) was reacted with 2,3-dihydroxynaphthalene (8.0 g) in methylene chloride in the presence of triethylamine. Aqueous hydrochloric acid was added to the reaction product to precipitate 3-chloroacetoxy-2-hydroxynaphthalene. The product was suction filtered and washed with methylene chloride.

3-chloroacetoxy-2-hydroxynaphthalene (2 g) was mixed with 2 g of 1,1-diphenyl-2-propyn-1-ol in benzene and heated to reflux in the presence of a catalytic amount of p-toluene sulfonic acid. After one hour, the reaction mixture was cooled and poured into dilute aqueous hydrochloric acid. The benzene layer was extracted with aqueous sodium hydroxide, washed with water and solvent removed on a rotary evaporator. The solid product was washed with a hexane/ether mixture and suction dried. NMR spectroscopy confirmed the product to be 5-chloroacetoxy-3,3-diphenyl-3H-naphtho[2,1-b]pyran. The product (2.1 g) had a melting point of 106°-108° C.

EXAMPLE 11

3-chloroacetoxy-2-hydroxynaphthalene (2 g) were mixed with 1,1-di-p-tolyl-2-propyn-1-ol (3 g) in benzene and the mixture heated slowly to reflux in the presence of a catalytic amount of toluene sulfonic acid. After about one hour, the reaction mixture was cooled, washed sequentially with dilute aqueous sodium hydroxide and water, and then dried. Benzene was removed on a rotary evaporator to give an oil that slowly crystallized. The crystals were slurried in a 3:1 hexane:ether mixture, filtered, and washed with a small amount of fresh hexane:diethyl ether and dried. The resultant product (2.7 g) was confirmed by NMR spectroscopy to be 5-chloroacetoxy-3,3-p-methylphenyl-3H-naphtho[2,1-b]pyran. The product had a melting point of 162°-163° C.

EXAMPLE 12

The naphthopyran compounds of Examples 1-11 were imbibed into separate polymerizates of poly[diethylene glycol bis(allyl carbonate)]. On exposure to ultraviolet light from a 365 nm lamp, the imbibed polymer samples elicited a photochromic response which faded on removal of the UV light source. The absorption maximums and fade rates of the compounds of Examples 1-11 are tabulated in Table I.

TABLE I

| Compound of Example | Absorption λ Max (NM) | Fade Rate[1] T ½, seconds |
|---|---|---|
| 1 | 455 | 81 |
| 2 | 440 | 94 |
| 3 | 483 | 63 |
| 4 | 483 | 210 |
| 5 | 447 | 138 |
| 6 | 446 | 100 |
| 7 | 467 | 82 |
| 8 | 434 | 96 |
| 9 | 470 | 134 |
| 10 | 458 | 96 |
| 11 | 476 | 105 |

[1] At Room Temperature

Although the present invention has been described with reference to the specific details of particular embodiments thereof, it is not intended that such details be regarded upon the scope of the invention except insofar as to the extent that they are included in the accompanying claims.

I claim:

1. A naphthopyran represented by the following graphic formula:

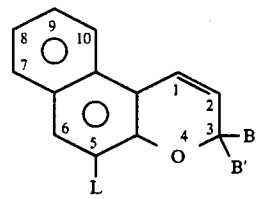

wherein

I. L is the group, —W—T(Z)=Xg, wherein
 (a) W is selected from the group consisting of the bivalent radicals,

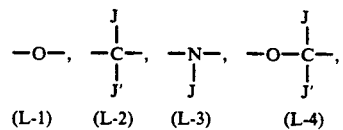

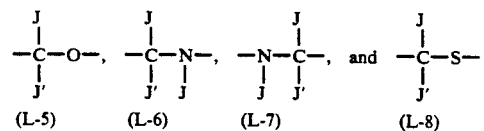

said J and J' each being selected from the group consisting of $C_1$–$C_4$ alkyl, or J and J' taken together is a single oxygen,
 (b) T is selected from the group consisting of carbon and sulfur,
 (c) X is selected from the group consisting of oxygen, sulfur and —N—J″, said J″ being selected from the group hydrogen, hydroxy, $C_1$–$C_4$ alkyl, $C_1$-$C_4$ alkoxy or $C_1$-$C_4$ alkenyl, or J" may combine with Z to form a pyridyl group
(d) Z is selected from the group consisting of hydrogen, $C_1$-$C_4$ alkyl, $C_1$-$C_4$ alkenyl, $C_1$-$C_4$ monohaloalkyl, $C_1$-$C_4$ alkoxy($C_1$-$C_4$)alkyl, amino, $C_1$-$C_4$ mono- or di-alkylamino, the unsubstituted and substituted aryl groups phenyl and naphthyl, and the unsubstituted and substituted heterocyclic groups pyridyl, thienyl, furyl, piperidinyl furfuryl, the aryl and heterocyclic substituents being selected from the group consisting of $C_1$-$C_4$ alkyl, $C_1$-$C_4$ monohaloalkyl, $C_1$-$C_4$ polyhaloalkyl, $C_1$-$C_4$ alkoxy($C_1$-$C_4$)alkyl, $C_1$-$C_4$ alkoxy and halogen, said halogen (or halo group) being fluorine or chlorine, and
(e) g is the integer 1 or 2 when X is sulfur and is the integer 1 when X is oxygen or —N—J", and II. B and B' are each selected from the group consisting of:
(a) the unsubstituted or substituted aryl groups phenyl and naphthyl,
(b) the unsubstituted or substituted heterocyclic groups pyridyl, thienyl, furyl, piperidinyl and furfuryl,
(c) $C_1$-$C_4$ alkyl, $C_1$-$C_4$ haloalkyl, $C_1$-$C_4$ alkoxy($C_1$-$C_4$)alkyl, $C_3$-$C_6$ cycloalkyl, $C_1$-$C_4$ alkoxy($C_3$-$C_6$) cycloalkyl, and halo $C_3$-$C_6$ cycloalkyl, said halo group being fluorine or chlorine, and
(d) B and B' may combine and taken together form the group, adamantylidene, the aryl group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, the heterocyclic group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, said halogen (or halo group) being fluorine or chlorine.

2. A naphthopyran represented by the following graphic formula:

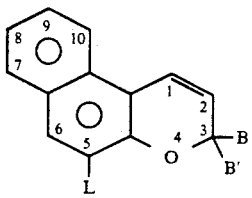

wherein,
I. L is the group, —W—T(Z)=Xg, wherein:
(a) W is selected from the group consisting of oxygen, carbon and nitrogen,
(b) T is carbon,
(c) X is oxygen,
(d) Z is selected from the group consisting of $C_1$-$C_4$ alkyl, $C_1$-$C_4$ monoalkylamino and phenyl, and
(e) g is the integer 1, and II. B and B' are each selected from the group consisting of:
(a) the unsubstituted or substituted aryl groups phenyl and naphthyl,
(b) the unsubstituted or substituted heterocyclic groups pyridyl, thienyl, furyl, piperidinyl and furfuryl,
(c) $C_1$-$C_4$ alkyl, $C_1$-$C_4$ haloalkyl, $C_1$-$C_4$ alkoxy($C_1$-$C_4$)alkyl, $C_3$-$C_6$ cycloalkyl, $C_1$-$C_4$ alkoxy($C_3$-$C_6$) cycloalkyl, and halo $C_3$-$C_6$ cycloalkyl, said halo group being fluorine or chlorine, and
(d) B and B' may combine and taken together form the group, adamantylidene, the aryl group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, the heterocyclic group substituents being selected from $C_1$-$C_4$ alkyl, $C_1$-$C_4$ haloalkyl, $C_1$-$C_4$ alkoxy, $C_1$-$C_4$($C_1$-$C_4$)alkyl and halogen, said halogen (or halo group) being fluorine or chlorine.

3. The naphthopyran of claim 2 wherein W is oxygen, Z is methyl, phenyl or methylamino.

4. The naphthopyran of claim 1 wherein L is acetoxy, benzoyloxy or methyl carbamyloxy.

5. The naphthopyran of claim 2 wherein B and B' are each selected from the group consisting of phenyl and substituted phenyl.

6. The naphthopyran of claim 5 wherein the substituted phenyl is mono- or di($C_1$-$C_4$)alkylphenyl, mono- or di-($C_1$-$C_4$)alkoxyphenyl, chlorophenyl or fluorophenyl.

7. The naphthopyran of claim 3 wherein B and B' are each selected from the group consisting of phenyl and substituted phenyl.

8. The naphthopyran of claim 7 wherein the substituted phenyl is mono- or di($C_1$-$C_4$)alkylphenyl, mono- or di-($C_1$-$C_4$)alkoxyphenyl, chlorophenyl and fluorophenyl.

9. The naphthopyran of claim 4 wherein B and B' are each selected from the group consisting of phenyl and substituted phenyl, said substituted phenyl being selected from mono- or di-($C_1$-$C_4$)alkylphenyl, mono- or di($C_1$-$C_4$)alkoxyphenyl, chlorophenyl or fluorophenyl.

10. 5-acetoxy-3(3,4-dimethoxyphenyl),3(2-fluorophenyl)-3H-naphtho[2,1-b]pyran.

11. 5-methylcarbamoyloxy-3(3,4-dimethoxyphenyl),3(2-fluorophenyl)-3H-naphtho[2,1-b]pyran.

12. 5-acetoxy-3,(4-methoxyphenyl),3(2-fluorophenyl)-3H-naphtho[2,1-b]pyran.

13. 5-acetoxy-3(3,4-dimethoxyphenyl)-3-phenyl-3H-naphtho[2,1-b]-pyran.

14. 5-acetoxy-3,3(4-methylphenyl)-3H-naphtho[2,1-b]pyran.

15. A photochromic article comprising a polymerized organic host material and a photochromic amount of a naphthopyran compound represented by the following graphic formula:

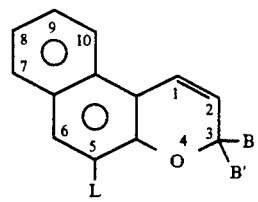

wherein,
I. L is the group, —W—T(Z)=Xg, wherein:
(a) W is selected from the group consisting of the bivalent radicals,

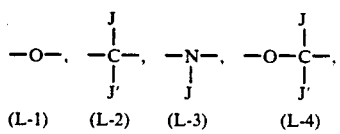

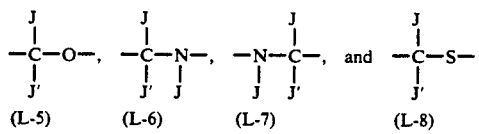

said J and J' being selected from the group consisting of $C_1$-$C_4$ alkyl, or J and J' taken together is a single oxygen, (b) T is selected from the group consisting of carbon and sulfur, (c) X is selected from the group consisting of oxygen, sulfur and -N-J", said J" being selected from the group hydrogen, hydroxy, $C_1$-$C_4$ alkyl, $C_1$-$C_4$ alkoxy or $C_1$-$C_4$ alkenyl, or J" may combine with Z to form pyridyl group, (d) Z is selected from the group consisting of hydrogen, $C_1$-$C_4$ alkyl, $C_1$-$C_4$ alkenyl, $C_1$-$C_4$ monohaloalkyl, $C_1$-$C_4$ alkoxy($C_1$-$C_4$)alkyl, amino, $C_1$-$C_4$ mono- or di-alkylamino, the unsubstituted and substituted aryl groups phenyl and naphthyl, and the unsubstituted and substituted heterocyclic groups pyridyl, thienyl, furyl, piperidinyl furfuryl, the aryl and heterocyclic substituents being selected from the group consisting of $C_1$-$C_4$ alkyl, $C_1$-$C_4$ monohaloalkyl, $C_1$-$C_4$ polyhaloalkyl, $C_1$-$C_4$ alkoxy($C_1$-$C_4$)alkyl, $C_1$-$C_4$ alkoxy and halogen, said halogen (or halo group) being fluorine or chlorine, and (e) g is the integer 1 or 2 when X is sulfur and is the integer 1 when X is oxygen or —N—J", and II. B and B' are each selected from the group consisting of:

(a) the unsubstituted or substituted aryl groups phenyl and naphthyl, (b) the unsubstituted or substituted heterocyclic groups pyridyl, thienyl, furyl, piperidinyl and furfuryl, (c) $C_1$-$C_4$ alkyl, $C_1$-$C_4$ haloalkyl, $C_1$-$C_4$ alkoxy($C_1$-$C_4$)alkyl, $C_3$-$C_6$ cycloalkyl, $C_1$-$C_4$ alkoxy($C_3$-$C_6$) cycloalkyl, and halo $C_3$-$C_6$ cycloalkyl, said halo group being fluorine or chlorine, and (d) B and B' may combine and taken together form the group, adamantylidene, the aryl group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, the heterocyclic group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, said halogen (or halo group) being fluorine or chlorine.

16. The photochromic article of claim 15 wherein the organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

17. A photochromic article comprising a polymerized organic host material and a photochromic amount of a naphthopyran compound represented by the following graphic formula:

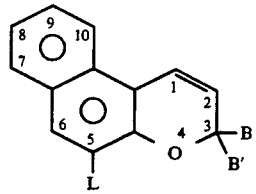

wherein

I. L is the group, —W—T(Z)=Xg, wherein:

(a) W is selected from the group consisting of oxygen, carbon and nitrogen, (b) T is carbon, (c) X is oxygen, (d) Z is selected from the group consisting of $C_1$-$C_4$ alkyl, $C_1$-$C_4$ monoalkylamino and phenyl, and (e) g is the integer 1, and II. B and B' are each selected from the group consisting of:

(a) the unsubstituted or substituted aryl groups phenyl and naphthyl, (b) the unsubstituted or substituted heterocyclic groups pyridyl, thienyl, furyl, piperidinyl and furfuryl, (c) $C_1$-$C_4$ alkyl, $C_1$-$C_4$ haloalkyl, $C_1$-$C_4$ alkoxy($C_1$-$C_4$)alkyl, $C_3$-$C_6$ cycloalkyl, $C_1$-$C_4$ alkoxy($C_3$-$C_6$) cycloalkyl, and halo $C_3$-$C_6$ cycloalkyl, said halo group being fluorine or chlorine, and (d) B and B' may combine and taken together form the group, adamantylidene, the aryl group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, the heterocyclic group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, said halogen (or halo group) being fluorine or chlorine, and said organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallyidene pentaerythritol.

18. The photochromic article of claim 16 wherein L is acetoxy, benzoyloxy or methyl carbamyloxy.

19. The photochromic article of claim 17 wherein B and B' are each selected from the group consisting of phenyl and substituted phenyl, said substituted phenyl being selected from mono- or di-($C_1$-$C_4$)alkylphenyl, mono- or di($C_1$-$C_4$)alkoxyphenyl, chlorophenyl or fluorophenyl.

20. The photochromic article of claim 19 wherein the organic host material is a solid transparent homopolymer or copolymer of diethylene glycol bis(allyl carbonate), poly(4,4'-dioxydiphenyl-2,2-propane), polymethylmethacrylate, or polyvinylbutyral.

21. The photochromic article of claim 20 wherein the photochromic compound is present in an amount of from about 0.01 to 20 weight percent.

22. The photochromic article of claim 21 wherein the article is a lens.

23. A photochromic article comprising a solid transparent polymerized organic host material and a photochromic amount of each of (a) a first photochromic substance selected from the group consisting of spiro(indolino) naphthoxazines, spiro(indolino) pyrido benzoxazines, and spiro(indolino) benzoxazines, and (b) a naphthopyran compound represented by the following graphic formula:

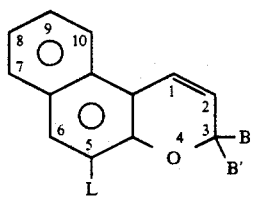

wherein,
I. L is the group, —W—T(Z)=Xg, wherein:
(a) W is selected from the group consisting of the bivalent radicals,

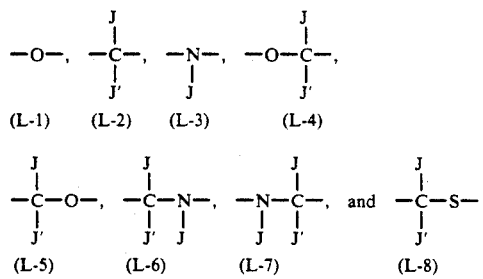

said J and J' each being selected from the group consisting of $C_1$-Chd alkyl, or J and J' taken together is a single oxygen,
(b) T is selected from the group consisting of carbon and sulfur,
(c) X is selected from the group consisting of oxygen, sulfur and —N—J", said J" being selected from the group hydrogen, hydroxy, $C_1$-$C_4$ alkyl, $C_1$-$C_4$ alkoxy or $C_1$-$C_4$ alkenyl, or J" may combine with Z to form a pyridyl group,
(d) Z is selected from the group consisting of hydrogen, $C_1$-$C_4$ alkyl, $C_1$-$C_4$ alkenyl, $C_1$-$C_4$ monohaloalkyl, $C_1$-$C_4$ alkoxy($C_1$-$C_4$)alkyl, amino, $C_1$-$C_4$ mono- or di-alkylamino, the unsubstituted and substituted aryl groups phenyl and naphthyl, and the unsubstituted and substituted heterocyclic groups pyridyl, thienyl, furyl, piperidinyl furfuryl, the aryl and heterocyclic substituents being selected from the group consisting of $C_1$-$C_4$ alkyl, $C_1$-$C_4$ monohaloalkyl, $C_1$-$C_4$ polyhaloalkyl, $C_1$-$C_4$ alkoxy($C_1$-$C_4$)alkyl, $C_1$-$C_4$ alkoxy and halogen, said halogen (or halo group) being fluorine or chlorine, and (e) g is the integer 1 or 2 when X is sulfur and is the integer 1 when X is oxygen or —N—J", and
II. B and B' are each selected from the group consisting of:
(a) the unsubstituted or substituted aryl groups phenyl and naphthyl,
(b) the unsubstituted or substituted heterocyclic groups pyridyl, thienyl, furyl, piperidinyl and furfuryl,
(c) $C_1$-$C_4$ alkyl, $C_1$-$C_4$ haloalkyl, $C_1$-$C_4$ alkoxy($C_1$-$C_4$)alkyl, $C_3$-$C_6$ cycloalkyl, $C_1$-$C_4$ alkoxy($C_3$-$C_6$) cycloalkyl, and halo $C_3$-$C_6$ cycloalkyl, said halo group being fluorine or chlorine, and
(d) B and B' may combine and taken together form the group, adamantylidene, the aryl group substituents $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, the heterocyclic group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, said halogen (or halo group) being fluorine or chlorine.

24. The photochromic article of claim 23 wherein the organic host material is selected from the group consisting of polymers of polyol(allyl carbonate) monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

25. A photochromic article comprising a solid transparent polymerized organic host material and a photochromic amount of each of (a) a first photochromic substance selected from the group consisting of spiro(indolino) naphthoxazines, spiro(indolino) pyrido benzoxazines, and spiro(indolino) benzoxazines, and (b) a naphthopyran compound represented by the following graphic formula:

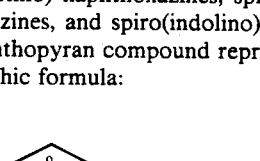

wherein,
I. L is the group, —W—T(Z)=Xg, wherein:
(a) W is selected from the group consisting of oxygen, carbon and nitrogen,
(b) T is carbon,
(c) X is oxygen,
(d) Z is selected from the group consisting of $C_1$-$C_4$ alkyl, $C_1$-$C_4$ monoalkylamino and phenyl,
(e) g is the integer 1, and
II. B and B' are each selected from the group consisting of:
(a) the unsubstituted or substituted aryl groups phenyl and naphthyl, (b) the unsubstituted or substituted heterocyclic groups pyridyl, thienyl, furyl, piperidinyl and furfuryl, (c) $C_1$-$C_4$ alkyl, $C_1$-$C_4$ haloalkyl, $C_1$-$C_4$ alkoxy($C_1$-$C_4$)alkyl, $C_3$-$C_6$ cycloalkyl, $C_1$-$C_4$ alkoxy($C_3$-$C_6$) cycloalkyl, and halo $C_3$-$C_6$ cycloalkyl, said halo group being fluorine or chlorine; and (d) B and B' may combine and taken together form the group, adamantylidene, the aryl group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, the heterocyclic group substituents being selected from $C_1$-$C_4$ alkyl, $C_1$-$C_4$ haloalkyl, $C_1$-$C_4$ alkoxy, $C_1$-$C_4$ alkoxy($C_1$-$C_4$)alkyl and halogen, said halogen (or halo group) being fluorine or chlorine, and wherein the organic host material is selected from the group consisting of polymers of polyol(allyl carbonate)monomer, polyacrylates, poly(alkylacrylates), polymers of polyfunctional acrylate monomers, cellulose acetate, cellulose triacetate, cellulose acetate propionate, cellulose acetate butyrate, poly(vinyl acetate), poly(vinyl alcohol), poly(vinyl chloride), poly(vinylidene chloride), polycarbonate, polyurethanes, poly(ethylene terephthalate), polystyrene, copoly(styrene-methylmethacrylate), copoly(styrene-acrylonitrile), polyvinylbutyral, and polymers of diallylidene pentaerythritol.

26. The photochromic article of claim 24 wherein L is acetoxy, benzoyloxy or methyl carbamyloxy.

27. The photochromic article of claim 2 wherein B and B' are each selected from the group consisting of phenyl and substituted phenyl, said substituted phenyl being selected from mono- or di-($C_1$-$C_4$)alkylphenyl, mono- or di($C_1$-$C_4$)alkoxyphenyl, chlorophenyl or fluorophenyl.

28. The photochromic article of claim 27 wherein the organic host material is a solid transparent homopolymer or copolymer of diethylene glycol bis(allyl carbonate), poly(4,4'-dioxydiphenol2,2-propane), polymethylmethacrylate, or polyvinylbutyral.

29. The photochromic article of claim 28 wherein the first photochromic substance is a spiro(indolino) pyrido benzoxazine or spiro(indolino) naphthoxazine.

30. The photochromic article of claim 28 wherein the first photochromic substance and photochromic naphthopyran compound are each present in amounts of from about 0.05 to about 10 weight percent.

31. The photochromic article of claim 30 wherein the weight ratio of the first photochromic substance to the naphthopyran compound varies from about 1:3 to about 3:1.

32. The photochromic article of claim 31 wherein the article is an ophthalmic lens.

* * * * *

UNITED STATES PATENT AND TRADEMARK OFFICE
CERTIFICATE OF CORRECTION

PATENT NO. : 5,244,602
DATED : September 14, 1993
INVENTOR(S) : Barry Van Gemert It is certified that error appears in the above-indentified patent and that said Letters Patent is hereby corrected as shown below:

Column 26, claim 2, line 10, "$C_1$-$C_4$($C_1$-$C_4$)alkyl" should be --$C_1$-$C_4$ alkoxy($C_1$-$C_4$)alkyl--.

Column 27, claim 15, line 23, "form pyridyl" should be --form a pyridyl--.

Column 29, claim 23, line 63, "piperidinyl furfuryl" should be --piperidinyl and furfuryl--.

Column 30, claim 23, line 16, "substituents $C_1$-$C_4$" should be --substituents being selected from $C_1$-$C_4$--.

Column 32, claim 27, line 5, "Claim 2" should be --claim 25--.

Signed and Sealed this

Sixth Day of September, 1994

Attest:

BRUCE LEHMAN

Attesting Officer     Commissioner of Patents and Trademarks